(12) United States Patent
Cleland et al.

(10) Patent No.: US 9,808,154 B2
(45) Date of Patent: Nov. 7, 2017

(54) BIOMETRIC IDENTIFICATION VIA RETINA SCANNING WITH LIVENESS DETECTION

(71) Applicant: Retina Biometrix, LLC, San Antonio, TX (US)

(72) Inventors: Timothy P. Cleland, San Antonio, TX (US); Nazariy Shaydyuk, San Antonio, TX (US)

( * ) Notice: Subject to any disclaimer, the term of this patent is extended or adjusted under 35 U.S.C. 154(b) by 0 days.

(21) Appl. No.: 14/861,984

(22) Filed: Sep. 22, 2015

(65) Prior Publication Data

US 2016/0012291 A1    Jan. 14, 2016

Related U.S. Application Data

(63) Continuation-in-part of application No. 14/837,892, filed on Aug. 27, 2015, which is a continuation of application No. 13/942,336, filed on Jul. 15, 2013, now abandoned.

(60) Provisional application No. 61/671,149, filed on Jul. 13, 2012.

(51) Int. Cl.
*G06K 9/00* (2006.01)
*A61B 3/12* (2006.01)

(52) U.S. Cl.
CPC ........ *A61B 3/1233* (2013.01); *G06K 9/00597* (2013.01); *G06K 9/00906* (2013.01)

(58) Field of Classification Search
None
See application file for complete search history.

(56) References Cited

U.S. PATENT DOCUMENTS

| 5,615,683 A * | 4/1997 | Toge | A61B 3/1233 600/479 |
| 7,284,859 B2 * | 10/2007 | Ferguson | A61B 3/1025 351/205 |
| 2003/0048929 A1 * | 3/2003 | Golden | A01K 11/008 382/115 |
| 2005/0232506 A1 * | 10/2005 | Smith | G06T 5/50 382/254 |

(Continued)

OTHER PUBLICATIONS

Laser speckle contrast imaging in biomedical optics, by Boas et al., Journal of biomedical optocs Jan./Feb. 2010 vol. 15(1), pp. 1-12.*

(Continued)

*Primary Examiner* — Vikkram Bali
(74) *Attorney, Agent, or Firm* — Jackson Walker LLP

(57) ABSTRACT

Various systems, processes, and techniques may be used to achieve biometric identification via retina scanning with liveness detection. In some implementations, systems, processes, and techniques may include the ability to scan a retina to acquire at least one retina image and analyze the image to identify retinal components. The systems, processes, and techniques may also include the ability to compute and compare the information about the identified retinal components with pre-stored information and determine whether the scanned retina is associated with the pre-stored information. The systems, processes, and techniques may further include the ability to determine whether the imaged retina is composed of live tissue. The security system may then perform a chain of actions based on the matching and live tissue results.

19 Claims, 8 Drawing Sheets

(56) References Cited

U.S. PATENT DOCUMENTS

| | | | | |
|---|---|---|---|---|
| 2006/0088193 A1* | 4/2006 | Muller | ............... | G06K 9/00597 |
| | | | | 382/117 |
| 2010/0098300 A1* | 4/2010 | Otto | ................... | G06K 9/00617 |
| | | | | 382/117 |
| 2012/0163678 A1* | 6/2012 | Du | ....................... | G06K 9/0061 |
| | | | | 382/117 |
| 2012/0328156 A1* | 12/2012 | Nakano | ................ | G06T 7/0083 |
| | | | | 382/103 |
| 2013/0268563 A1* | 10/2013 | Shiell | ..................... | G06F 17/30 |
| | | | | 707/797 |

OTHER PUBLICATIONS

Spectral imaging of the retina, by Mordant et al., EYE (2011) 25, 309-320.*

* cited by examiner

BIOMETRIC IDENTIFICATION VIA RETINA SCANNING WITH LIVENESS DETECTION

RELATED APPLICATIONS

This application is a continuation-in-part of U.S. patent application Ser. No. 14/837,892, entitled "Biometric Identification Via Retina Scanning" and filed on Aug. 27, 2015, which is a continuation of U.S. patent application Ser. No. 13/942,336, entitled "Biometric Identification Via Retina Scanning" and filed on Jul. 15, 2013, which claims priority to U.S. Patent Application No. 61/671,149, entitled "Non-Mydriatic Retinal Scanner For Biometric Identification" and was filed on Jul. 13, 2012. These prior applications are herein incorporated by reference in their entirety.

BACKGROUND

Biometrics is the use of distinctive biological and/or behavioral characteristics to identify an individual. Archeological evidence shows that the history of biometrics dates as early as 6,000 B.C., when human fingerprints were used to associate a person with an event or a transaction. The first modern wide-spread use of biometrics was the capture of hand images for use in identification, developed in 1858 by Sir William Herschel. Since then, biometric technology progressed quickly, and widespread use of fingerprint identification led to the development of automated fingerprint scanning and identifying systems. Presently, fingerprint identification is still the most common form of biometric identification used in the world. But many high security institutions such as the FBI, CIA, and NASA have recently employed iris scanning. Other biometric technologies that exist utilize speech, face, signature, and palm recognition.

Although fingerprint biometrics has proven effective, its public perception is weak, collection of high quality prints is difficult, and age and occupation can alter person's fingerprints. Moreover, images of fingerprints can also be fabricated and used to spoof security systems. Face recognition was thought to be a good means of identification, but facial recognition is sensitive to changes in light and expression, people's faces change over time, and the current technology in facial recognition produces a lot of false positives. Voice recognition could have been effective because the sensors (e.g., microphones) are easily available, but sensor and channel variances are difficult to control. Recently, iris scanning has been thought to be the best solution because the iris is protected by the cornea and believed to be stable over an individual's lifetime. However, iris scanners are thought to be easily fooled by fake-iris contact lenses.

An idea to use retina vasculature patterns for personnel authentication originated from the work of Dr. Carleton Simon and Dr. Isodore Goldstein, published in the New York State Journal of Medicine in 1935. Every eye, including those of identical twins, has its own unique pattern of blood vessels, allowing for accurate identification. Image acquisition for retina scanning was very impractical and expensive back then; however, today, fundoscopes and other ocular cameras are regularly used by medical professionals to image the retina. In fundoscopy, illumination is flooded onto the retinal surface with (filtered) incandescent or flash light source(s). The illuminated portion of the retina that falls into the field of view of the device is re-imaged by optics onto an image sensor, and then converted into a digital image.

SUMMARY

Various systems, processes, and techniques may be used to achieve biometric identification via retina scanning with liveness detection. In general, the identification system would automatically acquire at least one retinal image, preferably in a non-mydriatic fashion, analyze the information from the image and determine how close it matches the previously stored information, and, possibly, perform a set of actions based on the matching results.

In some implementations, a process for biometric identification via retina scanning and liveness detection may include scanning a retina to acquire at least one retinal image, processing the image to extract desired physiological components (e.g., retinal blood vessels, optic disk, fovea, branch point locations, and/or other structural components) and use this information to compare/differentiate against pre-stored information for a previously imaged retina. These processes may be implemented in an integrated system including an imaging device, a computer, and/or other standalone image acquisition and processing devices, which may include hardware and/or software components for executing one or more of the operations.

In certain implementations, illumination of a retina by the imaging device may involve laser light source(s) of particular wavelength(s), the choice of which would depend on the desired physiological features to be imaged. The acquired image(s) could be then manipulated in a way to enhance the features of interest and facilitate their extraction.

Some implementations may include additional image acquisition device such as image processing and analysis techniques to assess the extent of "liveness" of the scanned retina. This could be an additional security measure used to prevent "spoofing," a significant disadvantage associated with other biometric identification systems. Examples of living tissue confirmation could be detecting the presence of blood flow within the retinal vessels in a periodic and predictable vascular pulsation, coincident with a beating heart. These features are more difficult to fabricate and confirmation of their presence would allow an indication of whether the imaged tissue was live or a fake image or a reproduction.

In some implementations, whether the acquired image could belong to a known individual, can be based on both the matching results of the detected components as well as the presence of a pre-determined minimum number of verified signs of "liveness". Based on the conclusion of authenticity, the security system could evoke a pre-determined set of actions.

Various other features will be apparent to those skilled in the art from the following detailed description and the accompanying figures and claims.

DETAILED DESCRIPTION

Figure 1:
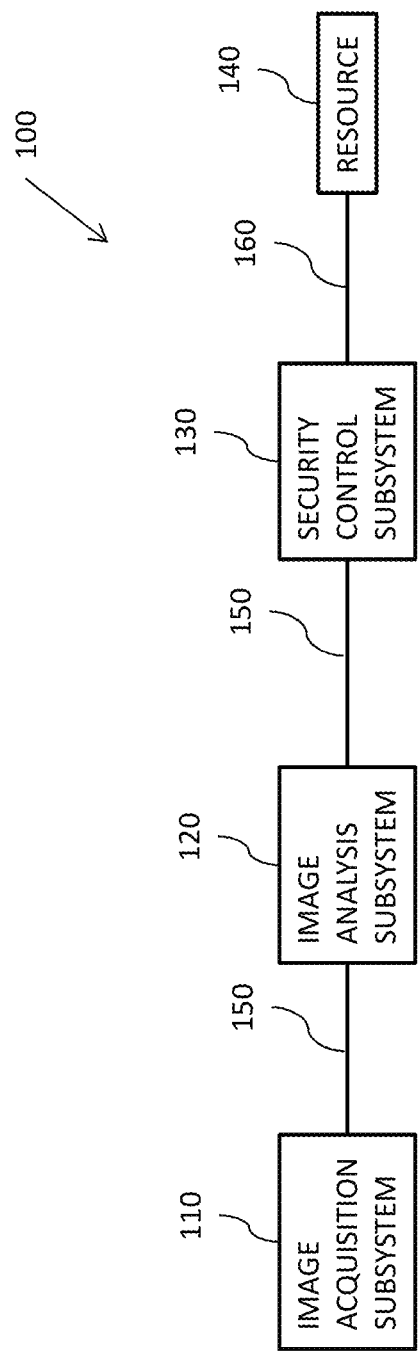
FIG. 1 is a block diagram illustrating selected components of an example system for biometric identification via retina scanning.

FIG. 1 illustrates a general block diagram of an example system 100 for biometric identification via retina scanning with liveness detection. As shown, system 100 includes an image acquisition subsystem 110, an image analysis subsystem 120, a security control subsystem 130, and a resource 140.

Image acquisition subsystem 110 includes the light source(s), sensor(s) and other optical components for imaging a retina. The light sources may, for example, be lasers or light-emitting diodes (LEDs), and the sensors may, for example, be charge-coupled devices (CCDs), arranged in linear and/or planar manners. The light sources may operate in various ranges of the electromagnetic spectrum (e.g., infrared, red, green, or blue) to acquire images of the retina and to detect live tissue ("liveness detection"). The images and liveness data may, for example, be determined by fundoscopy, scanning laser ophthalmoscopy, optical coherence tomography, Laser Doppler flowmetry, and laser speckle contrast imaging.

In certain implementations, only one light source may be used. In other implementations, multiple light sources may be used. The light sources and associated image sensors and detectors may or may not require pupil dilation to acquire the images.

Image acquisition subsystem 110 may include the optics required to illuminate the retina and to focus the reflected light on the image detector(s). Also, additional light sources, optics, and sensors for external eye illumination, viewing, and fixation may be included in this subsystem. In general, image acquisition subsystem 110 may include a variety of optical elements, including light sources (e.g., lasers or LEDs), lenses (e.g., collimator, relay, objective and focusing,), filters (e.g., band-pass), mirrors (e.g., apertured, dichroic, spinning, or motorized), image rotators, image stabilizers, moving opto-mechanical assemblies with motors and control electronics to ensure desired illumination and imaging conditions.

Image analysis subsystem 120 is responsible for analyzing the image(s) acquired by image acquisition subsystem 110 and determining whether the imaged retina is associated with a retina that has been previously imaged (e.g., previously stored in a secure database) and whether or not the imaged retina is alive ("liveness detection"). Image analysis subsystem 120 may, for example, include one or more processors (e.g., microprocessors), microcontrollers, ASICs, and memory for processing and storing instructions and data. Image analysis subsystem 120 may be a single computer (e.g., laptop, desktop, workstation, etc.), a collection of computers (e.g., coupled together by a network), a stand-alone electronic unit, or a combination—thereof, including all necessary hardware and software.

In particular implementations, image analysis subsystem 120 may have multiple functions. For example, image analysis may include procedures involving image processing, features extraction, features analysis, data matching, and other data manipulation techniques.

Image processing may provide image manipulation procedures to resolve physiologic structures in the image. Example procedures include de-noising, edge/feature enhancement, contrast enhancement, uneven illumination compensation, and other techniques that help emphasize physiologic structures in the image.

Features extraction may separate useful physiological components and structures (e.g., retinal blood vessels) from the image background. Additionally, features extraction may segment on smaller subunits (e.g., vessel segments, branch points, and/or vessel orientation).

Features analysis may determine data regarding components. For example, features analysis may determine the spatial relationship between various retina components (e.g., blood vessels, optic disc and fovea). Additionally, features analysis may determine data about one or more components (e.g., vessel segment length and location, branch points, number of branches, segment orientation, vein, artery, pulse rate, and others). The data regarding the features may be stored in a database that can be used to compare/differentiate between subjects. Data matching may perform a series of data comparison steps to assess the extent of similarity/difference between the newly extracted physiologic components and those stored in the database.

For instance, image analysis subsystem 120 may compare a newly calculated data set against a pre-stored data set associated with a particular subject. Determining whether the calculated data set corresponds to the pre-stored data set may, for example, be accomplished by determining whether a number of components or subcomponents (e.g., branch points) between the data sets correspond. Techniques for determining whether a calculated data set for imaged branch points corresponds to a pre-stored data set are discussed in more detail below.

As mentioned previously, image analysis subsystem 120 may also determine whether the imaged retina is alive. For example, image analysis subsystem 120 may determine whether blood is flowing in the retinal blood vessels, perhaps in a pulsatile fashion coincident with a beating heart, and/or whether oxygenated or deoxygenated blood is flowing in the retinal blood vessels. Determining whether there is blood flowing in the retina may be accomplished using a variety of techniques. For example, Laser Doppler Flowmetry (LDF) or speckle contrast imaging may be used.

In LDF, a frequency shift that arises in light that has been scattered by moving red blood cells may be measured to obtain a quantification of blood cell movement. For instance, by illuminating a tissue sample with single-frequency light and processing the frequency distribution of the backscattered light, an estimate of the blood perfusion can be achieved. Because LDF typically uses a narrow beam, the targeting of the laser may be based on the vasculature determined from the image. In certain implementations, the measurements may be made at points at which blood flow is expected (e.g., on blood vessels) and at points at which blood flow is not expected (e.g., off blood vessels).

In speckle contrast imaging, when an object is illuminated with coherent light, a speckle pattern, or random interference pattern, is produced at the camera due to the fact that the light reaching each pixel has traveled slightly different path lengths and added coherently, both constructively and destructively. The dynamics of the speckle pattern contain information about the motion of the scattering particles in the sample. When some of the scattering particles are in motion (i.e., blood cells), the speckle pattern fluctuates in time. When the exposure time of the sensor is longer than the time scale of the speckle intensity fluctuations (typically less than 1 ms for biological tissues), the camera integrates the intensity variations, resulting in blurring of the speckle pattern. In areas of increased motion, there is more blurring of the speckles during the camera exposure, resulting in a lower spatial contrast of the speckles in these areas.

Given that the retina is a highly scattering tissue, the speckle contrast imaging method is a suitable way to detect blood flow in retinal vessels. The retina would serve as a stationary surface, whereas the moving particles (i.e., red blood cells) would be a dynamically changing scattering medium.

To determine whether the imaged retina is alive, image analysis subsystem 120 may use a variety of techniques. For example, image analysis subsystem 120 may simply determine that there is blood flow in the retinal vasculature. As another example, image analysis subsystem 120 may determine whether the blood flow is over an elongated path (e.g., a substantial length of a blood vessel), which would make spoofing more difficult. As an additional example, image analysis subsystem 120 may determine whether there is blood flow in multiple vessels, possibly with branches, which would help to reduce spoofing. As a further example, image analysis system 120 may develop a set of blood vessels based on the blood flow and attempt to match them to the vessels obtained from the retina image and/or from the pre-stored data set (e.g., based on branch points). As another example, the verification of "liveness" could be based on the presence of pulsatile blood flow in selected vessel(s).

Another example of determining whether an imaged retina is composed of live tissue is determining whether the imaged retina contains physiologic blood flow in the retinal veins and/or arteries. In detail, images can be obtained by image acquisition subsystem 110 in a way to create a contrast between vessels caring oxygenated and deoxygenated blood (i.e., arteries or veins). Given the different light absorption characteristics for oxy- and deoxyhemoglobin in red blood cells, for example, a retina can be first illuminated with wavelengths at which absorption characteristics differ substantially for the two kinds of hemoglobin. The resulting images will then have one type of vessel (artery or vein) more apparent than the other. Additionally, a control image may be obtained by using a wavelength which is fairly equally absorbed by oxy- and deoxyhemoglobin. The resulting images can be added/subtracted (e.g., via union, intersection, complementation) to contain only the desired type of vessels. Consequently, the extracted vessels can be classified as arteries or veins. Some implementations may allow undefined type of vessels which fail to be classified.

By verifying that the imaged retina has physiologic blood flow in the retinal veins and arteries, a determination can be made as to whether imaged retina is alive. In certain implementations, the verification can be extended. For example, the vein/artery map may be compared to the determined blood vessel map to determine a correspondence. Additionally, the vein/artery map could be verified against previously stored information. These classifications may be performed at the time a user registers with the system by scanning with similar wavelengths to those user during verification.

If the calculated data set for the imaged retina corresponds to a pre-stored data set and blood is flowing in the retina, indicating that the currently scanned retina corresponds to a previously scanned retina and is alive, image analysis subsystem 120 may generate a message for security control subsystem 130. The message may, for example, be a control signal or an instruction. Based on the message from image analysis subsystem 120, security control subsystem 130 may grant a user access.

Security control subsystem 130 is responsible for granting access to resource 140 in case of a positive outcome, that is, if image analysis subsystem 120 determines that the currently scanned retina is associated with a retina that has already been registered with system 100 and was proven to be live tissue. Security control system 130 may, for example, grant physical access or electronic access. For instance, resource 140 may be a building, and security control system 130 may grant access to an entrance (e.g., a door) of the building, by, for example, unlocking the entrance. For instance, security control subsystem 130 may include an electromagnetic lock that would unlock if the data matching algorithm detects a match and blood is flowing. As another example, resource 140 may be other computer hardware (e.g., a computer system or database) or software (e.g., an application), and security control system 130 may grant access to the hardware or software.

Image acquisition subsystem 110, image analysis subsystem 120, and security control subsystem 130 are coupled together by links 150. Links 150 may be busses, wires, cables, fiber-optic cables, or legs of a communication network (e.g., portions of a LAN, a WAN, or the Internet). Links 150 may be physical (e.g., cables, busses, wires, fiber-optic cables) or non-physical (e.g., Radio Frequency (RF) or infrared (IR)). Thus, image acquisition subsystem 110, image analysis subsystem 120, and security control subsystem 130 may or may not be physically coupled to each other and may be located near or far from each other, or be integrated in a single unit. Security control subsystem 130 may be coupled to resource 140 by a physical, an electronic, or an instruction link 160.

In particular implementations, image acquisition subsystem 110 includes a non-mydriatic retina imager and a non-mydriatic blood flow imager. The retina imager is operable to generate an image of a retina (e.g., blood vessels, optic disc, macula, and peripheral retina). The blood flow imager is operable to generate an image of blood flowing in the retina blood vessels, from which "liveness" may be detected and determined.

The retina imager may, for example, obtain retina images by means of line scanning laser technology. The measuring laser beam may, for instance, may form a spot conjugate with the fundus of the eye to be examined. The optics may then reform the reflected light into a complementary line that defines the reflectivity profile of the illuminated region and then focus the image onto a sensor. Sweeping the laser line across the retina surface allows collection of reflection intensity profiles (e.g., in a linear CCD device, possibly after being enlarged by an optical lens), which are then further reconstructed into an aerial reflection profile. In particular implementations, the retina imager may generate multiple images of the retina—in the red spectrum, in the green spectrum, and/or in the blue spectrum.

The blood flow imager is able to generate an image of blood flowing in the retina. In particular, the blood flow imager may obtain relative blood flow profiles in the retinal vasculature, which can be mapped to retina blood vessels. In particular implementations, the blood flow imager may use speckle contrast imaging to develop an image of a retina's blood flow. In speckle contrast imaging, the accumulation of scattered light (e.g., from a laser) off a surface produces a random interference, or speckle, pattern. Blurring of the speckle pattern is caused by moving particles (i.e., red blood cells) and can, if desired, be quantified to measure the flow.

Since speckle contrast imaging is dependent on particles in motion, it may double as both a vasculature detection technique and a mechanism for blood flow recognition.

The blood flow imager may, for example, illuminate the preferred retina surface with diffuse laser light—for example, by directing infrared light (e.g., from a semiconductor laser source) through a collimator lens and an objective lens. The back-scattered light from the retina surface again passes through the objective lens and enters an observation optical system, perhaps via an image stabilizer. The light is then focused on a sensor (e.g., a CCD array) to capture the speckle pattern of the illuminated area. The retinal blood vessels may be identified at the locations of decreased speckle contrast.

The light for the laser speckle imaging may, for instance, be generated from a standard scanning laser ophthalmoscope or from an additional laser incorporated therewith. Light in the infrared could, for example, be used. The light could be generated from any number of standard lasers. The scattered light could, for example, be detected with a standard detector (e.g., CMOS or CCD). If incorporated into a scanning laser ophthalmoscope, a bimodal imaging modality could be achieved.

In certain modes of operation, image acquisition subsystem 110 scans an eye to acquire at least one image of the retina and an image of the blood flowing therethrough. In some implementations, retina images may be generated in the red spectrum, the green spectrum, and the blue spectrum, and blood flow may be imaged in the infrared spectrum. The image(s) may then be conveyed to image analysis subsystem 120, which may process the retina image(s) to identify retinal blood vessels. Techniques for identifying retina blood vessels are discussed in more detail below.

Image analysis subsystem 120 may also identify branch points of the retina blood vessels. Identifying branch points may, for example, be accomplished by analyzing a blood vessel to see if it contains a bifurcation. Image analysis subsystem 120 may also calculate a data set that represents the identified retinal vessel branch points. The data set may, for example, be based on the spatial orientation of the branch points relative to a point (e.g., in polar coordinates) or the geometries between branch points (e.g., distances to nearest neighbors). Techniques for identifying branch points and representing branch points in a data set are discussed in more detail below.

System 100 has a variety of features. For example, by using a scanning laser technology, the retina image may be acquired in a non-mydriatic manner. Traditional retina cameras, like a fundoscope, typically require a large pupil diameter (5 millimeters or greater), which may only be achieved using eye drops to dilate the pupil. In system 100, a pupil diameter of about 2.0 mm may be used. Although this degree of pupil dilation may not obtain as wide of a field of view and, hence, have less information, this is typically more comfortable to users, provides much quicker processing, and allows for very little, if any, recovery time on the part of the user. Moreover, fundoscopes typically require a technician to assist in imaging the retina, but users of system 100 may not require any assistance. The system may include the necessary user-system interface for automatic alignment. Additionally, using laser scanning technology to acquire retinal images allows for more efficient illumination and light collection, small depth of focus, scattered light suppression, and lower light intensities, resulting in a better image quality and patient comfort.

Compared to other types of biometric identification systems, system 100 is significantly more difficult to fool. The retina is embedded deep within a body organ, making it more difficult with which to tamper. Additionally, because of the special requirements of the imaging process, it cannot be imaged without a subject's consent. Additionally, liveness detection (e.g., retinal blood flow recognition) may also be used to differentiate between living tissue and non-living duplicates.

Therefore, a combination of the available imaging methods could be used to implement a system that would automatically acquire retinal images and extract meaningful physiological information, such as the presence or absence of blood vessels, bifurcation locations, the presence or absence of blood flow, and other uniqueness markers, which could be then used as identity authentication.

Biometric identification via retina scanning with liveness detection may have a variety of applications. For example, it could be used in financial transactions. Additionally, the healthcare system is ranked second only to the financial system when it comes to biometric identification. Today, more and more hospitals and companies are implementing biometric identification techniques for security purposes and patient records. As the healthcare system switches from a paper-based system to an electronic one, biometric identification will slowly become one of the best ways of tracking records.

Although FIG. 1 illustrates one implementation of a system for biometric identification via retina scanning, other such systems may include fewer, additional, and/or a different arrangement of components. For example, image analysis subsystem 120 could be incorporated into image acquisition subsystem 110. As another example, security control subsystem 130 may be part of image analysis subsystem 120. For instance, the security control subsystem may grant access to processing capabilities, applications, and/or data on image analysis subsystem 120. As an additional example, several deferent modalities of retina imaging techniques could be used to obtain desired identification information (i.e. fundoscopy, scanning laser ophthalmoscopy, optical coherence tomography, Doppler flowmetry, and laser speckle contrast imaging).

As another example, a system may include a subject accommodation subsystem, which is adapted to receive and stabilize a user's head. For instance, a subject accommodation subsystem may include a headrest and eye alignment and focusing devices. Feedback regarding head and eye alignment may be provided to the user by aural and visual techniques.

As an additional example, an image acquisition subsystem may include a machine vision subsystem that obtains images external to the eye. These images may be used to calculate the spatial location of subject's eye relative to the device. This subsystem may contain image sensor(s) and associated optics for real-time position monitoring and auto-focusing. Additionally, a fixation point source may be used to ensure proper eye alignment.

As a further example, the system 100 may include a data monitoring capability, which performs data acquisition and/or error detection/correction. For example, laser control and steering circuitry, image sensor interface circuitry, signal conditioning and digitization, and other support circuitry for successful data acquisition and error detection/correction may be included.

As an additional example, a system may include an electro-mechanical control subsystem, which is responsible for aligning the optical axis of the user's eye with the device's optical axis. An electro-mechanical control subsystem may use a combination of electrical circuitry and mechanical servomotors to perform the alignment. The information from a machine vision subunit may be processed in an image analysis subsystem, and appropriate signals sent to the motorized chassis for eye-device position adjustment.

Figure 2:
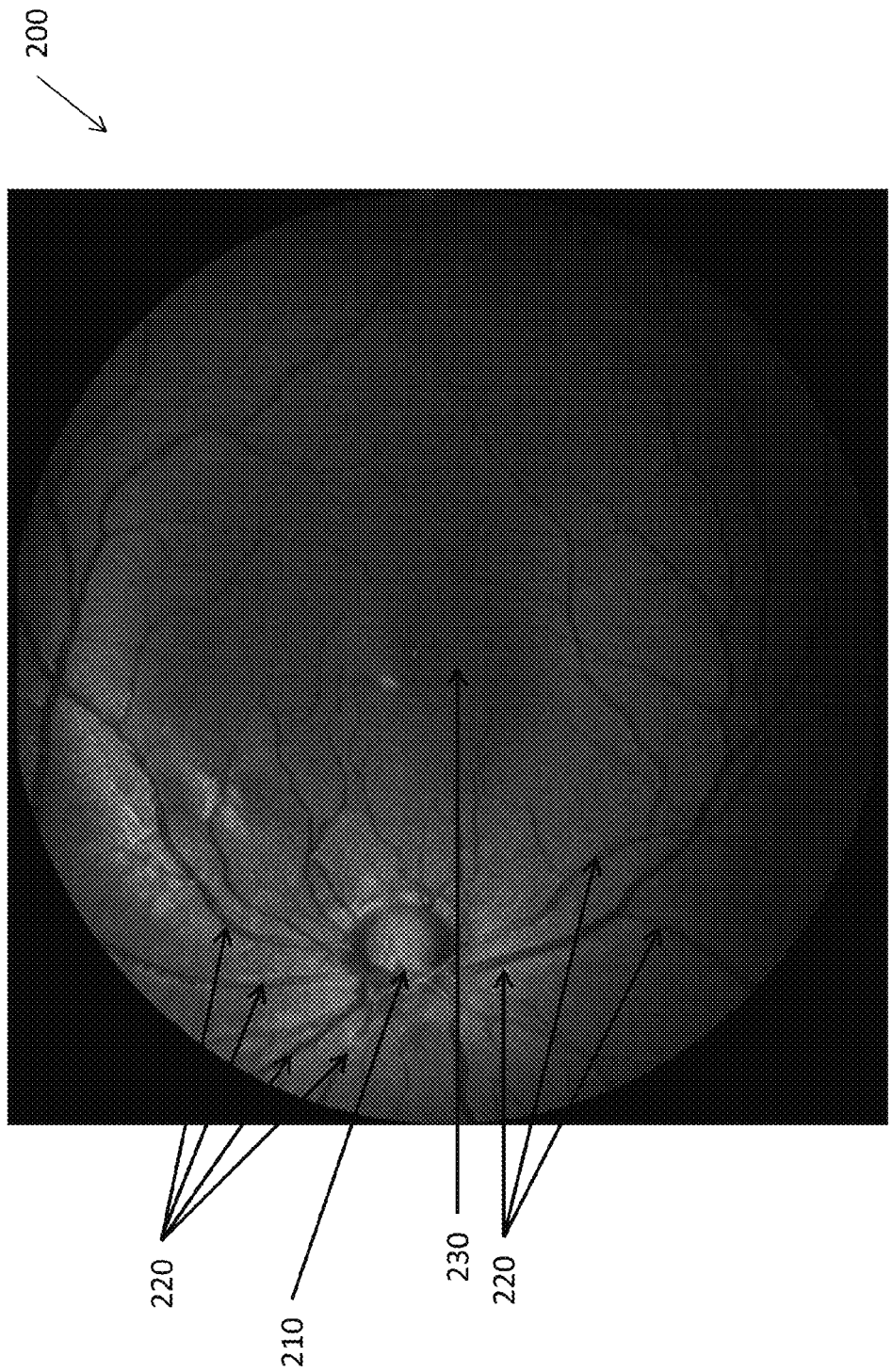
FIG. 2 is an image of a retina taken with a scanning laser ophthalmoscope.

FIG. 2 illustrates an example retina image 200. As seen in FIG. 2, the retina typically contains an optic disc 210 and a plurality of blood vessels 220. Image 200 also identifies the macula, which is located in the center spot, contains a fovea 230.

Figure 3:
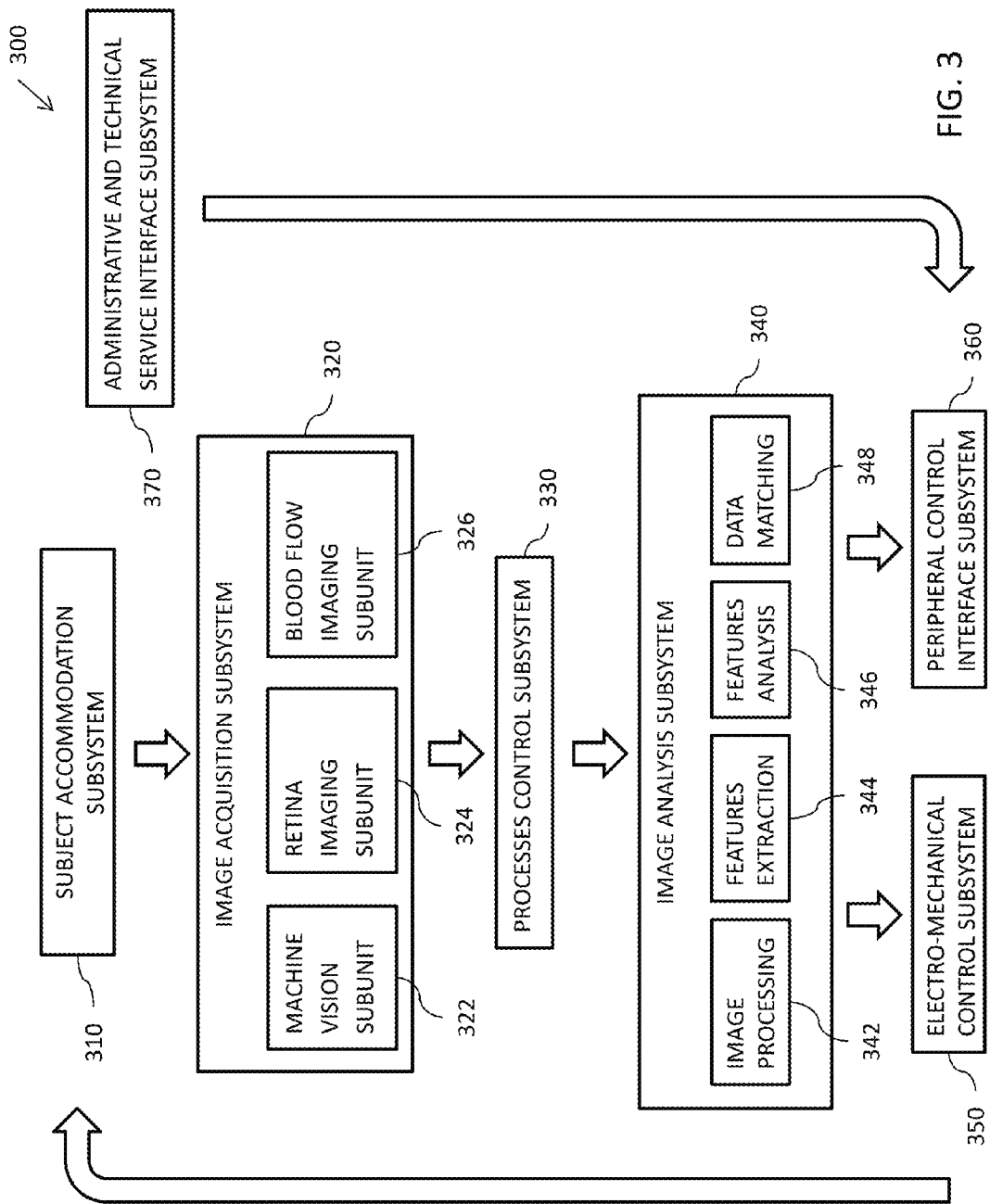
FIG. 3 is a block diagram illustrating selected components of an example system for biometric identification via retina scanning.

FIG. 3 illustrates another example system 300 for biometric identification via retina scanning with liveness detection. System 300 may, for example, represent an expanded description of one or more portions of system 100. Among other things, system 300 includes a subject accommodation subsystem 310, an image acquisition subsystem 320, a processes control subsystem 330, an image analysis subsystem 340, and an electro-mechanical control subsystem 350.

Subject accommodation subsystem 310 includes elements designed and adapted to receive and stabilize a user's head. In certain implementations, subject accommodation subsystem 310 may include a headrest, ambient light shields, and other devices and processes required for an eye-system alignment. Feedback regarding head and eye alignment, may be provided to the user by aural and visual techniques. Additional features of subsystem 310 may include a user control interface to aid in eye-system alignment, image acquisition triggering, or other actions that would facilitate automatic or semi-automatic system performance.

Image acquisition subsystem 320 includes the integration of light sources, optics, and sensors used to obtain external and internal images of an eye. The image acquisition subsystem 320 may include a variety of optical, mechanical, and electronic elements, as well as any additional components necessary for proper image acquisition. In the illustrated implementation, image acquisition subsystem 320 is divided into three subunits—machine vision subunit 322, retina imaging subunit 324, and blood flow imaging subunit 326, but one or more of these may be a part of the same unit.

Machine vision subunit 322 obtains images external to the eye. The images are used to calculate the spatial location of a subject's eye relative to the device. This allows continuous eye tracking, real-time position monitoring and autofocusing. The subsystem may contain image sensor(s), light sources and associated optics, or share the components with the other units. Additionally, a fixation source (e.g., a point source) may be used to ensure eye stabilization.

Retina imaging subunit 324 may, for example, obtain retina images by means of flying point or line scanning laser technology in a non-mydriatic fashion. The imaging system may focus a laser beam in a way as to form a spot or a thin line conjugate with the fundus of the eye to be examined. The optics may then reform the reflected light into a complementary point or line that defines the reflectivity profile of the illuminated region and then focus this light onto a sensor. Sweeping the laser point or the line across the retina surface allows collection of reflection intensity profiles, which are then further combined to form an aerial reflection profile.

In particular implementations, subunit 324 may generate one or a sequence of retinal images while illuminating the retina with light source(s) of one or several wavelengths, successively or simultaneously. Due to unique interactions of retinal tissue with particular wavelengths of light, the acquired images might contain different information—for instance, some features might be more apparent than other. Typical examples of physiological features are blood vessels, optic disc, and macula.

Previously published studies indicate the foveal region, for example, is most prominent (details best imaged) when illuminated with light from the blue spectrum. Furthermore, the blood vessels absorb more light from the blue spectrum, and thus, the images have good contrast between the vessels and the background. Similarly, the optic disc is most visible when illuminated with the light from the red portion of the spectrum. It is also known that specific types of proteins within the retina exhibit auto-fluorescence when illuminated with certain wavelengths (i.e., 488 nm and 580 nm). Thus, light absorption in vessels and light emission from the proteins in the background could enhance the image contrast.

Similarly, retinal reflectivity is greater for light from the near-infrared spectrum. More light can be reflected back into the imaging system, increasing the system's signal-to-noise ratio.

In addition, infrared waves are virtually invisible to the human eye and therefore, are unlikely to cause discomfort during image acquisition.

The laser sources used in scanning laser ophthalmoscopy typically include wavelengths from blue, green, red, and near-infrared parts of the spectrum. In particular, 488 nm, 532 nm and 785 nm laser sources are known to be used in some commercially available laser scanning ophthalmoscopes (SLOs). Therefore, some implementations might include laser source(s) with wavelength(s) chosen to provide the best contrast images of desired retinal elements.

Blood flow imaging subunit 326 is, for example, designed to detect the presence or absence of blood flow in the retinal blood vessels. In particular, subunit 326 may obtain information which can be used to calculate relative or absolute blood flow profiles in the retina, which, in turn, can be mapped into a retinal blood vessel network. In particular implementations, subunit 326 may use speckle contrast imaging, laser Doppler flowmetry, or vein/artery differentiation methods to develop an image map of a retina's blood flow.

Speckle contrast imaging may be utilized for blood flow detection and simultaneously be used as a vasculature detection technique. It is a mechanism to verify the presence or absence of blood flow in the imaged area, since it is dependent on individual red blood cells in motion.

Subunit 326 may, for example, illuminate the preferred area of retinal surface with diffuse laser light—for example, by directing infrared light (e.g., from a semiconductor laser source) with the help of optical elements. The back-scattered light from the retina surface again would pass through the objective lens and enter the observation optical system, perhaps via an image stabilizer. The light would then be focused on an image sensor (e.g., a CCD array) to capture the speckle pattern of the illuminated area. The data from the raw speckle image(s) could then be statistically manipulated to calculate local contrasts across the image and then converted into the relative blood flow map.

Time-integrated speckle imaging relies on the principle that the motion of the scattering particles (e.g., blood cells) is encoded in the dynamics of the speckle pattern, and blood flow can be associated with the blurring of the speckle pattern. Such spatial blurring may, for example, be measured by calculating the speckle contrast, K, defined as the ratio of the standard deviation, $\sigma_s$, to the mean intensity of pixel values, $<I>$, in a small region of the image, $$K(T)=\sigma_s(T)<I>$$

where T is the exposure time of the camera (multi-exposure imaging may be applied). The speckle contrast is, therefore, a measure of the local spatial contrast in the speckle pattern. A spatially resolved map of local speckle contrast can be calculated from a raw speckle image by computing this ratio at each point (e.g., pixel) in the image from the pixels in a surrounding N×N region, (typically N=7). Alternatively, the temporal speckle contrast may be calculated to detect flow using series of images. In this approach, the statistical analysis is performed on the corresponding pixels taken from n number of subsequent images. In either case, the theoretical speckle contrast has values between 0 and 1. A speckle contrast of 1 indicates that there is no blurring of the speckle pattern and, therefore, no flow, while a speckle contrast of 0 means that the scatterers (blood cells) are moving with sufficient speed enough to "average" the speckle background. The combination of spatial, multi-exposure and temporal speckle contrast imaging may be performed to improve the quality of the images.

The imaging unit 324 may perform the function of laser speckle imaging under certain conditions with limited results (e.g., when no area flow map is required). Consequently, a bimodal imaging unit could be achieved alleviating the need for system 326.

An alternative implementation of "liveness" detection by blood flow may use the laser Doppler flowmetry method. This technique measures absolute flow of a fluid using Doppler shift of a laser beam randomly scattered from stationary and moving particles. In this application, the absolute retinal blood flow could be detected at a particular location within the retina veins and arteries. To make the results more meaningful, the measurements may be performed by choosing coordinates of specifically selected locations where retinal blood flow or no retinal blood flow is expected. Thus, the expected locations would be defined from the image(s) obtained by subunit 324, and then compared with the flow/no flow locations obtained by subunit 326.

The processes control subsystem 330 provides a means of communication between individual electronic subunits that ensure a synchronized system. The subsystem may be partially implemented in some or all the electronic or mechanical units (i.e., clock oscillators, laser control and steering circuitry, image sensor interface circuitry, signal acquisition and processing circuitry, switches, and other support circuitry for successful data acquisition and error detection/correction) that are able to generate and/or react to event signal(s). The subsystem may or may not be a separate entity.

Image analysis subsystem 340 is divided into variety of discrete procedures involving image processing, feature extraction, feature analysis, and matching, and other data manipulation techniques. In the illustrated implementation, image analysis subsystem 340 has four major components—an image processing subunit 342, a features extraction subunit 344, a features analysis subunit 346, and a data matching subunit 348.

Image processing subunit 342 provides image manipulation procedures to resolve physiologic structures in the image. Example procedures include de-noising, edge/feature detection and enhancement, contrast enhancement, uneven illumination compensation, and other techniques to emphasize physiologic structures in the image.

Features extraction subunit 344 finds and separates desired physiological components (e.g., retinal vessels) from the image background. Additionally, these physiologic components may be resolved further into smaller subcomponents (e.g., vessel segments and branch points).

The features analysis subunit 346 computes and groups the relevant information about extracted physiologic components that can be used to compare/differentiate between subjects. It may also have a function to store the data, when needed. For example, the branch point locations for retina blood vessels and their spatial associations may be computed and stored. Additionally, the unit 346 may also analyze images to perform "liveness detection" (e.g., using speckle contrast, vein/artery recognition, etc.).

Data matching subunit 348 performs a series of data comparison steps to assess the extent of similarity/difference between the newly extracted physiologic structures and those stored in the secure database.

Data matching may assume several different approaches depending on the variety of underlying conditions. First, it may perform subject identification. In this mode, the calculated data set of the imaged subject may be compared to the data sets of all subjects stored in a database. Second, it may assist in addition of a new subject to the database. In this mode, the calculated data set may also be assessed across the entire database to ensure no individual with such data has been already added. Third, the matching procedure can perform subject authentication. In this mode, the calculated data may be compared to only the pre-stored data of an individual claimed to be the imaged subject. Thus, the subject may be presented by typing-in the name, ID number, and/or some other identifier to initiate the claim. Alternatively, the subject may be introduced by swiping the ID card, or verbally, if the system is equipped with the ID reader or speech recognition respectively.

Electro-mechanical control subsystem 350 is responsible for aligning the optical axis of the subject's eye with the device's optical axis. Electro-mechanical control subsystem 350 may use a combination of electrical circuitry and mechanical servomotors to align the chassis. The information from machine vision subunit 322 is processed in the image processing subsystem 342 and appropriate signals are sent to the motorized chassis for eye-device position adjustment. Subsystem 350 may also carry a function of ametropic correction by providing opto-mechanical focusing.

System 300 also includes a peripheral control interface subsystem 360 and an administrative and technical interface subsystem 370. Peripheral control interface subsystem 360 may be application specific and can be custom designed for end-user requirements. Based on the output of the data matching algorithms (match/no match) and "liveness" detection (live/not live), the device can send commands (e.g., signals or instructions) to other peripheral devices such as an electromagnetic lock, a motor, or an electrical switch.

Administrative and technical service interface subsystem 370 allows administrative control of the device, such as database manipulation including subject addition, subject deletion, and database merging. The interface also allows other technical services such as calibration, software update, and emergency control.

Parameters may also be calculated for other features of the imaged retina. For example, additional data may be generated regarding other types of components, such as branch segments. Branch segments may be found during the process of component extraction (e.g., when branch points are located). A branch segment may be defined as a part of a vessel connecting two branch points. Primary and terminal branches may be defined by a branch point and a terminal point, or even classified as terminal segments. Consequently, they may be described by several types of parameters: linking branch points, vessel segment neighbors, segment lengths (i.e., number of pixels forming thinned vessel segment). If reference points are available, the segments may be further described in terms of relative location, orientation (i.e., a direction of a vector defined by the two end points of a segment), and others.

Some system implementations that involve blood blow identification or vessel classification of arteries and veins may provide additional parameters, further diversifying the description information among individuals. Once all the parameter sets for all components of interest have been processed, they may be combined into a data set for further comparison and/or storage.

Figure 4:
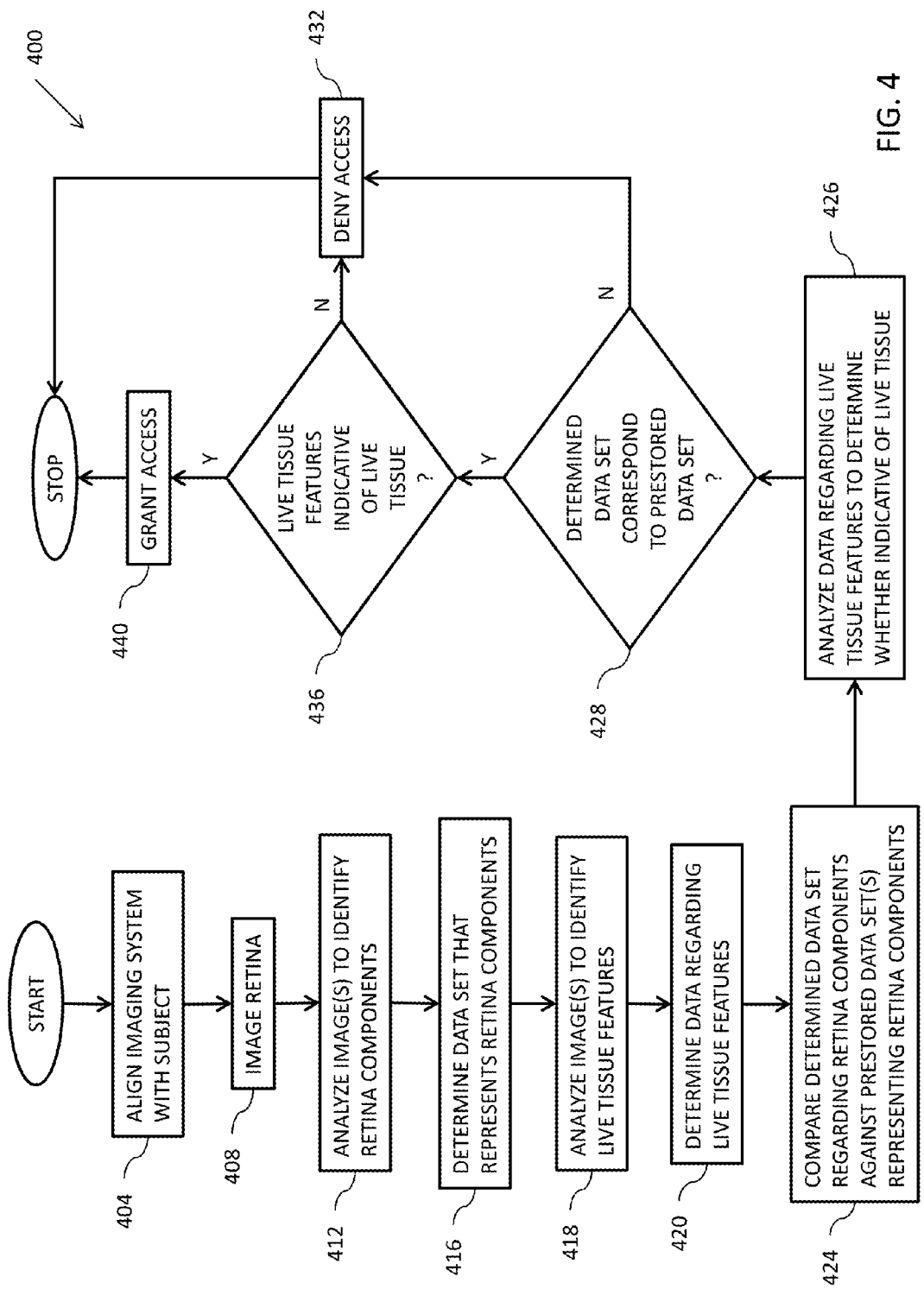
FIG. 4 is a flowchart illustrating selected operations of an example process for biometric identification via retina scanning.

FIG. 4 is a flowchart illustrating an example process 400 for biometric identification via retina scanning with liveness detection. Process 400 may, for example, be implemented and included by a system similar to system 100 and may expand upon selected operations thereof.

Process 400 calls for aligning an imaging system with a subject (operation 404). This may, for example, be accomplished by measuring the distance to the subject and/or by obtaining images external to the eye (e.g., via an infrared laser) and calculating the spatial location of a subject's eye relative to the device. A fixation point source may be used to ensure proper eye alignment.

In certain modes of operation, the system may acknowledge the presence of a subject and adjust its position relative to the subject, as required. The user detection could be implemented using infrared motion detectors and/or external/internal cameras, which could recognize (an outline of) a human, a human head, or an eye. Alternatively, the system could be activated with a voice or a "start" button. The position adjustment could be based, for example, on localization of a pupil (e.g., its outline or the center point).

Process 400 also calls for imaging the subject's retina (e.g., using a scanning laser ophthalmoscope or a fundoscope) to acquire at least one image thereof (operation 408), as previously described. In some implementations, images of the retina may be produced in multiple spectrums (e.g., the red spectrum, the green spectrum, and/or the blue spectrum).

Process 400 additionally calls for analyzing the retina image(s) to identify retina components (operation 412). The retina components may, for example, include retina blood vessels, the optic disc, and/or the fovea. Identifying retina components may, for example, include identifying a plurality of branch points of the retina blood vessels. Identifying a plurality of branch points may, for example, be accomplished by analyzing a blood vessel to determine whether it contains a bifurcation. For example, blood vessels in an image could be thinned to a standard width (e.g., one pixel) and then analyzed as to whether there are sufficient pixels around a point for a bifurcation to have occurred. For instance, in cases in which the blood vessels were thinned to one pixel in width, if a pixel had three neighboring pixels, a bifurcation would be indicated.

Process 400 further calls for determining a data set that represents the retina components (operation 416). For example, a data set may then be calculated that represents the identified retina branch points. The data set may, for instance, be based on the spatial orientation of the branch points relative to each other, to a reference point (e.g., fovea), or geometries between branch points (e.g., retinal vessel segment length and orientation).

The complexity of operation 416 depends on the availability of the components acquired from the operation 412 and the type of descriptive information to be calculated. For instance, the identified vasculature network could be segmented on separate branches and physical and statistical information could be calculated (i.e. position, lengths, quantities, spatial orientation, and interconnectivity). Similar information could be calculated for identified bifurcations. If optical coherence tomography used for image acquisition, the component's description information may become more complex (e.g., three dimensional), due to additional dimension, providing extra uniqueness.

Process 400 further calls for analyzing the image(s) to identify live tissue features (operation 418). The live tissue features may, for example, include the presence of flow, the presence of pulsatile flow, whether oxygenated and/or deoxygenated blood is flowing in the retinal blood vessels. The identification and extraction of each type of component or feature may require a series of specific image manipulations, examples of which are described further in text. Identifying blood flow in the retina may, for example, be accomplished analyzing blur patterns in a speckled image.

Process 400 also calls for determining data regarding the live tissue features (operation 420). Live tissue features may, for example, include the maps of blood flow in the retina, which could be compared against a previously derived map or against a blood vessel network. Another live tissue feature is a map of veins/arteries. This map may be compared against a previously derived vein/artery map or against a blood vessel network.

In detail, the image(s) can be obtained in a way to create a contrast between vessels caring oxygenated and deoxygenated blood (i.e. arteries and veins). Given different light absorption characteristics for oxy- and deoxyhemoglobin in red blood cells, a retina can be first illuminated with a wavelength at which absorption characteristics differ substantially for oxygenated or deoxygenated hemoglobin. The resulting images will then have one type of vessels more apparent than the other. Then, a control image might be obtained by using a wavelength that is equally absorbed by oxy- and deoxyhemoglobin. The resulting images can be added/subtracted (i.e. via union, intersection, complementation) to contain only the desired type of vessels. Consequently, the extracted vessels can be classified as arteries or veins. Some implementations may allow undefined type of vessels which fail to be classified.

Process 400 additionally calls for comparing the determined data set against at least one pre-stored data set representing retina components (operation 424). Comparing the determined data set against at least one pre-stored data set may, for example, be accomplished by determining whether the data for a component in one set corresponds to the data for a point in another set.

Process 400 further calls for analyzing the data regarding the live tissue features to determine whether it is indicative of living tissue (operation 426). Thus, it may be determined whether the imaged object (presumably a retina) was alive based on the detection of signs intrinsic to live tissue. This may, for example, be accomplished by analyzing a speckle contrast image to determine whether blurring is occurring along continuous paths, indicating the presence of retinal blood vessels. As an example, a flow map (e.g., a vascular map derived under positive blood flow conditions) could be compared to a vascular map obtained via a separate imaging modality (e.g., laser scanning imaging).

Alternatively, the verification of "liveness" could be based on the presence of pulsatile blood flow in selected vessel(s). The sequence of retinal images would be collected to capture at least one period of the blood flow cycle (i.e. several seconds/several heartbeats) and the changes of the blood flow velocity could be measured at certain locations to verify cyclic (physiologic) fluctuations of blood flow over the acquisition time.

Process 400 also calls for determining whether the calculated data set corresponds to a pre-stored data set (operation 428). Determining whether the calculated data set corresponds to the pre-stored data set may, for example, be accomplished by determining whether a number of branch points between the data sets correspond.

If the calculated data set does not correspond to a pre-stored data set, process 400 calls for denying access (operation 432), and process 400 is at an end. Denying access may, for example, include maintaining a lock for a physical facility or denying access to a computer resource (e.g., hardware, software, and/or data).

If, however, the determined data set corresponds to the pre-stored data set, process 400 calls for determining whether the live tissue features (liveness detection) are indicative of live tissue (operation 436). For example, this may be accomplished by determining whether blood is flowing the retina blood vessels.

If the live tissue features (liveness detection) are not indicative of live tissue, process 400 calls for denying access (operation 432). If, however, the live tissue features are indicative of live tissue, process 400 calls for granting access (operation 440). Granting access may, for example, include deactivating a lock for a physical facility or allowing access to a computer resource (e.g., hardware, software, and/or data). Process 400 is then at an end.

Although FIG. 4 illustrates an example process for biometric identification via retina scanning with liveness detection, other processes for biometric identification via retina scanning with liveness detection may include fewer, additional, and/or a different arrangement of operations. For example, a process may include operations to generate a pre-stored data set (e.g., by scanning an eye and performing component identification when a user registers for a security system). As another example, a message may be provided to a user (e.g., through audio or visual techniques) indicating the results of a comparison. As a further example, the imaging operations may be performed in an order (e.g., live tissue image first and retina image second), the analysis operations may be performed in a different order, and the access operations may be performed in a different order (e.g., live tissue features determination first).

Figure 5:
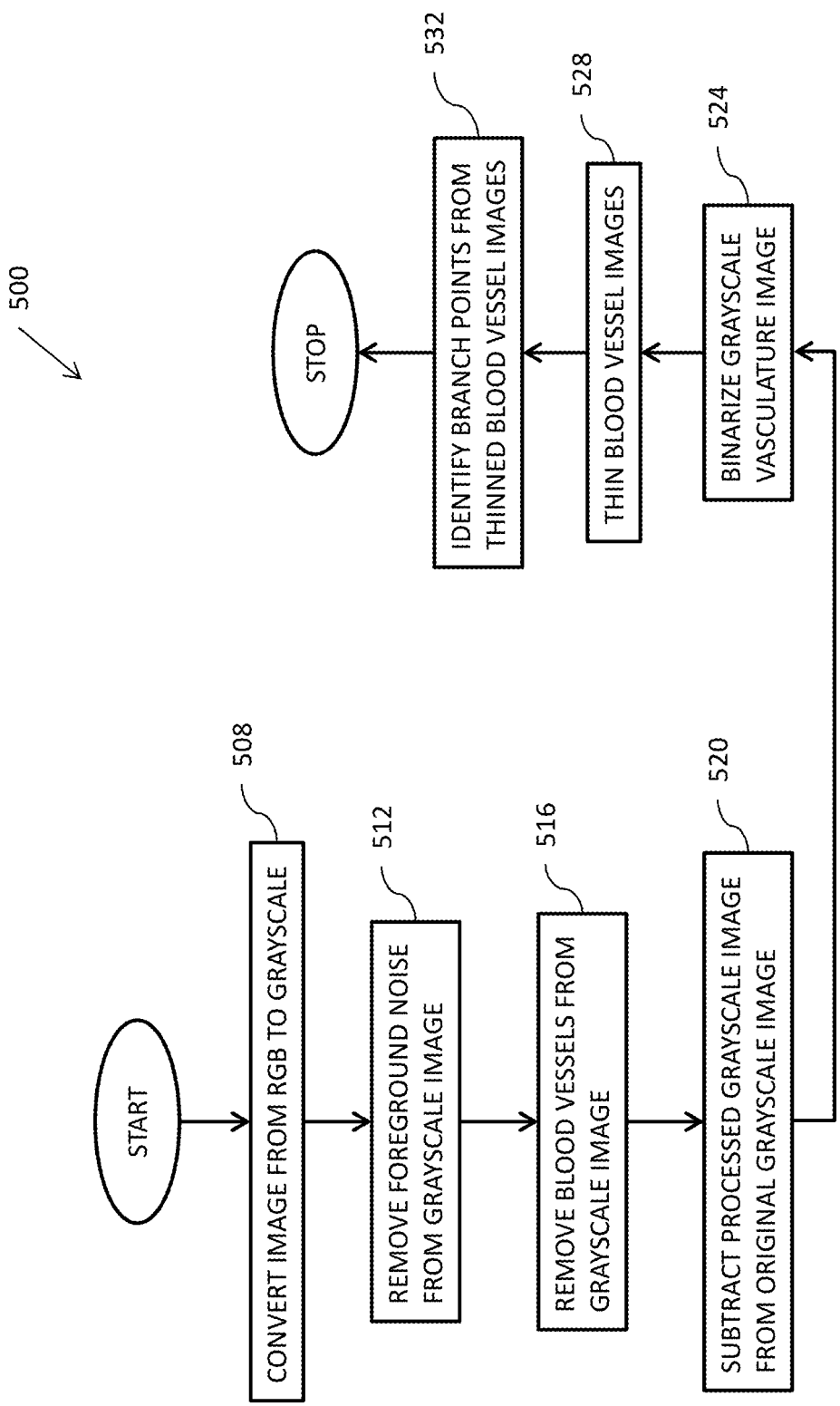
FIG. 5 is a flowchart illustrating selected operations of another example process for extracting retina blood vessel data.

FIG. 5 is a flowchart illustrating an example process 500 for extracting retina blood vessel data. Process 500 may, for example, be implemented by a system similar to image analysis subsystem 120 in system 100 or subsystem 344 in system 300 and may expand upon select operations thereof.

Process 500 calls for converting retina images from RGB to grayscale (operation 508). For example, a colored retina image may be converted to grayscale by applying the following formula:

Grayscale=0.3×*R*+0.59×*G*+0.11×*B*

Process 500 also calls for removing foreground noise from the grayscale image (operation 512). Removing the foreground noise may, for example, be accomplished by applying a morphological opening operator, which may remove small noise.

Process 500 further calls for removing the blood vessels from the grayscale image (operation 516). Removing the blood vessels may, for example, be accomplished by applying a morphological closing operator. At this point, the image should contain only the background.

Process 500 then calls for subtracting the processed grayscale image from the original grayscale image (operation 520), which should generate an image that displays only the vasculature. This may, for example, be performed by a matrix subtraction, which may be executed with a top-hat transformation.

Process 500 further calls for converting the grayscale vasculature image to a binary image (operation 524). This may, for example, be accomplished using a threshold value calculated from the image's gray-level intensity histogram. For example, the binarizing threshold could be set to 0.5, with pixel values below 0.5 set to 0 (black) while values above 0.5 are set to 1 (white). Binarization makes future calculations simpler to compute and pixels easier to evaluate by allowing mathematical morphing functions to be used.

Process 500 further calls for thinning the blood vessel images (operation 528). The vessel images may, for example, be thinned to one pixel in width by evaluating each pixel and their neighbors. This function thins the blood vessels to facilitate the detection of branch points since the weight of the widths of the blood vessels vary. For instance, on a 3×3 grid where the center is the pixel being evaluated, if three or more neighboring pixels are part of a branch, then the value of the evaluated pixel will be altered to the background color.

Process 500 also calls for determining the branch points (operation 532). This may, for example, be performed by evaluating the neighbors of each pixel. For instance, at each pixel with a value of 1, if there are three or more neighboring pixels with the same value, a branch point is located.

Although FIG. 5 illustrates a process for extracting retina blood vessel data, other processes for extracting retina blood vessel data may include fewer, additional, and/or a different arrangement of operations. As an example, a process may not convert an RBG image to grayscale (e.g., the image may already be in grayscale). As a further example, a process may perform a series of black-and-white morphological operations to clean up a black and white image.

Figure 6:
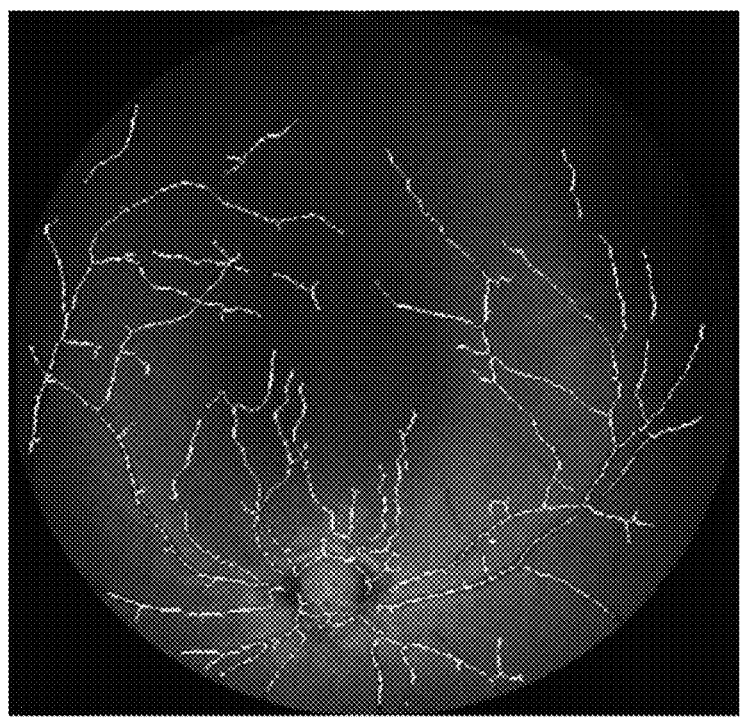
FIG. 6 illustrates blood vessel patterns determined for the retina image in FIG. 2

FIG. 6 shows the blood vessels extracted from retina image 200 by process 500. The image shows the binarized thinned vascular skeleton overlaid on the original greyscale image.

Figure 7:
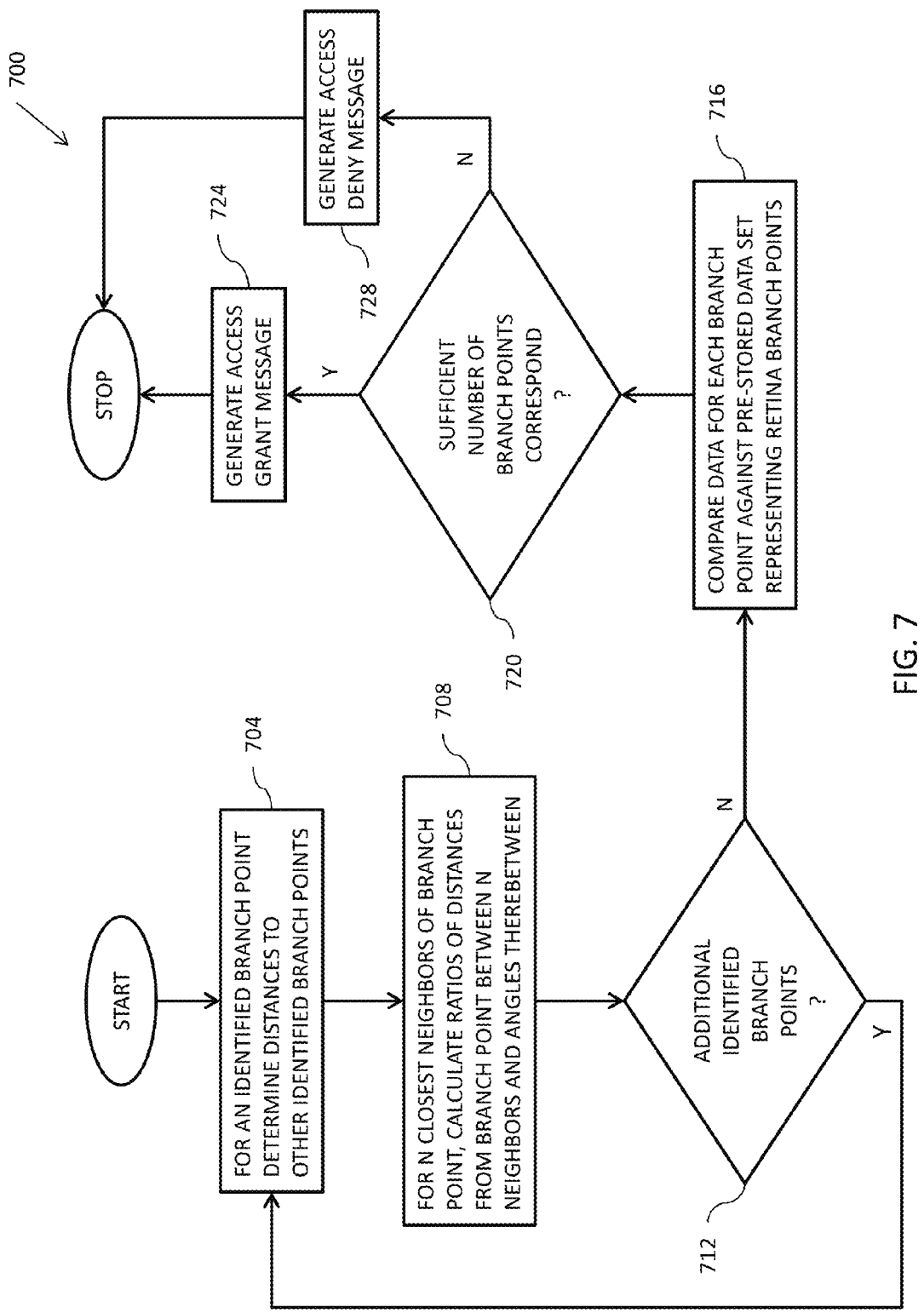
FIG. 7 is a flowchart illustrating select operations of an example process for determining whether data for a number of retina branch points is associated with a pre-stored data set for a number of branch points.

FIG. 7 is a flowchart illustrating and expanding upon select operations of system 100. Example process 700 is included to further describe the method by which a determination is made whether a set of data (regarding a number of retina branch points) is associated with another set of data. Process 700 may be used with a number of algorithms that determine branch point location and may, for example, be performed by a system similar to image analysis subsystem 120 in system 100.

In general, process 700 calculates ratios of relational Euclidean distances of neighboring branch points to compare two branch points. In particular, the ratios of the distances from the neighboring branch points to the branch points of interest and the angles between the neighboring branch points are used. The parameters calculated using this process are independent of translational, rotational, and scaled image variations, and thus, do not require reference points (i.e. fovea and optic disc).

Process 700 calls for determining distances from an identified branch point to the other identified branch points (operation 704). Determine distances between branch points may, for example, be accomplished with standard scaling and magnitude calculations.

Process 700 also calls for calculating a predetermined number of closest neighbors of the branch point being analyzed, ratios of distances from the branch point to the closest neighbors and the angles between the neighbors (operation 708). The distances may, for example, be computed with standard magnitude calculations, and the angles may be completed with standard vector calculations.

Process 700 also calls for determining whether there are additional identified branch points (operation 712). If there is another identified branch point, process 700 calls for determining the distances from the next identified branch point to the other identified branch points (operation 704) and computing the distance ratios and angles between a number of the closest neighbors (operation 708) for the next branch point. Operations 704-712 may be performed until all of the identified branch points have been processed.

Process 700 also calls for comparing the data for each branch point against one or more pre-stored data sets representing retinal branch points (operation 716). An example algorithm for the data comparison procedure may be broken up into two phases. The first phase of the algorithm may be based on comparing the data sets, whereas the second phase may decide whether the amount of matched information between the two sets is sufficient to be considered as a subject match. The data sets may be compared in terms of the parameters of the components (i.e. parameter by parameter, component by component).

The fact that the parameters of the two points compare in their values, however, does not guarantee that they are necessarily the same. Therefore, such pairs of similar points may be further evaluated to distinguish the true matched pairs from points that only share some common parameter values. That is, each pair contains a true point, taken from the pre-stored data, and a candidate point—a point from the input image that shares similar features with the true point. If the candidate point is found in the vicinity of the true point (set by a threshold radius r), the two points are considered to be the same. Tolerance between potentially corresponding points can be set to provide a stricter or more relaxed comparison metrics.

Phase two of the comparison algorithm determines whether a sufficient number of components (e.g., branch points, vessel segment length, and segment angle orientation) correspond with each other to constitute a match.

If a sufficient number of retinal components correspond between the two data sets, process 700 calls for generating a grant access message (operation 724). The message may, for example, be a signal to a device and/or an indication to the user. As mentioned previously, the access may be to a physical location (e.g., a room or building) or a non-physical location (e.g., a computer system). Process 700 is then at an end.

If a sufficient number of retinal components do not correspond between the two data sets, however, process 700 calls for generating a deny access message (operation 728). Denying access may, for example, include informing the user that they are being denied access and/or generating an alert (e.g., an alarm signal and/or a message). Process 700 is then at an end.

As will be appreciated by one skilled in the art, aspects of the present disclosure may be implemented as a system, method, or computer program product. Accordingly, aspects of the present disclosure may take the form of an entirely hardware environment, an entirely software embodiment (including firmware, resident software, micro-code, etc.), or an implementation combining software and hardware aspects that may all generally be referred to herein as a "circuit," "module," or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of a computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be a tangible medium that can contain or store a program for use by or in connection with an instruction execution system, apparatus, or device.

A computer readable signal medium may include a propagated data signal with computer readable program code embodied therein, for example in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any medium, including but not limited to wireless, wireline, optical fiber cable, RF, etc. or any suitable combination of the foregoing.

Computer program code for carrying out operations for aspects of the disclosure may be written in any combination of one or more programming languages such as Java, Smalltalk, C++ or the like and conventional procedural programming languages, such as the "C" programming language, hardware description languages, such as VHDL, or similar programming languages.

The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Alternatively, the software may be stored and executed entirely within the mobile independent stand-alone security system.

Aspects of the disclosure are described below with reference to flowchart illustrations and/or block diagrams of methods, apparatus (systems), and computer program products according to implementations. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other device to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions that execute on the computer or other programmable apparatus provide processes for implementing the functions/acts specified in the flowchart and/or block diagram block or blocks.

Figure 8:
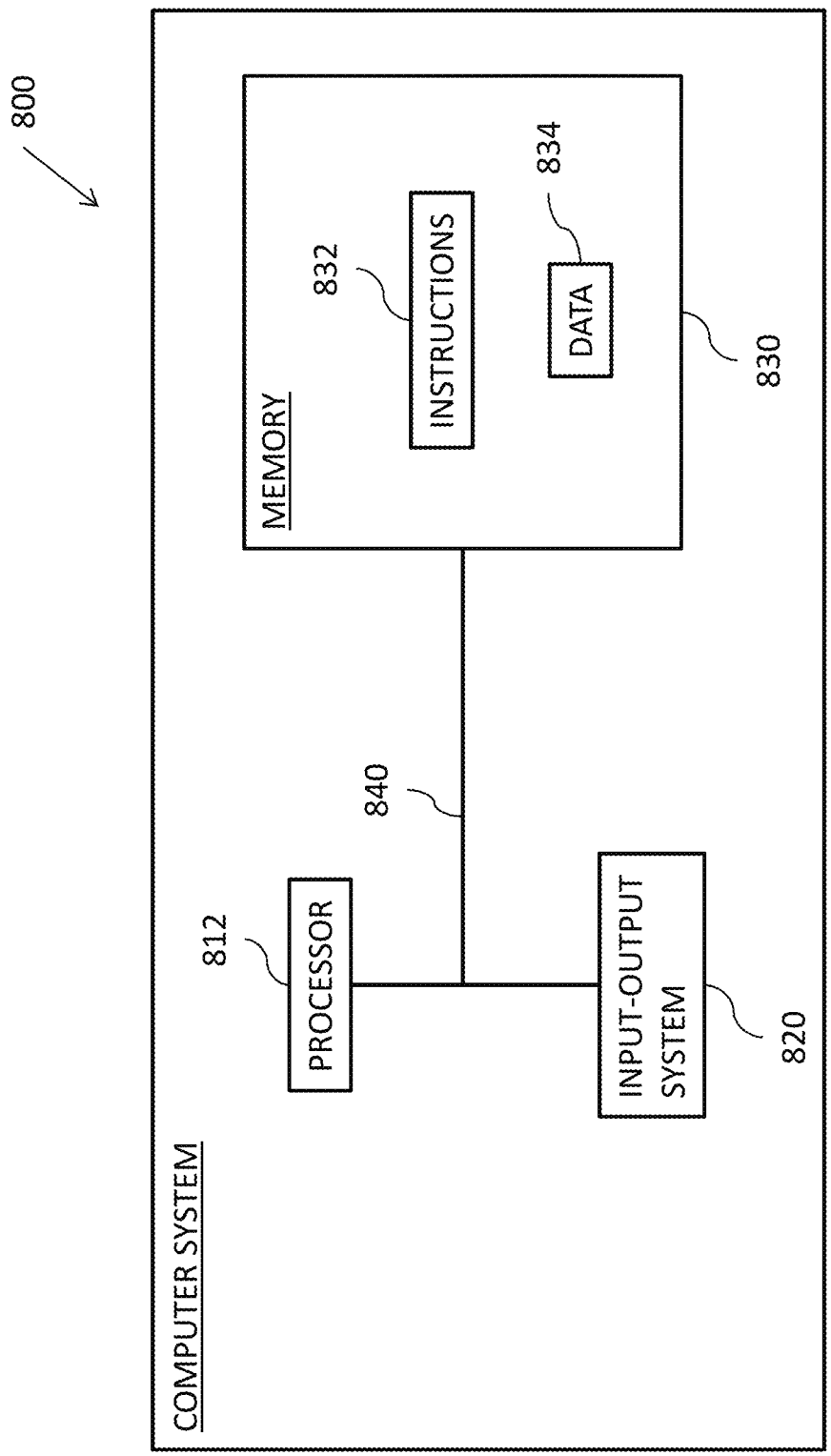
FIG. 8 is a block diagram illustrating selected components of an example computer system for biometric identification via retina scanning.

FIG. 8 illustrates selected components of an example computer system 800 for performing biometric identification via retina scanning with liveness detection. System 800 may, for example, be part of an ophthalmoscope, located locally with an ophthalmoscope, or located remotely located from an ophthalmoscope. System 800 includes a processor 810, an input-output system 820, and memory 830, which are coupled together by a network system 840.

Processor 810 may, for example, be a microprocessor, which could, for instance, operate according to reduced instruction set computer (RISC) or complex instruction set computer (CISC) principles. In general, processor 810 may be any device that manipulates information in a logical manner.

Input-output system 820 may, for example, include one or more communication interfaces and/or one or more user interfaces. A communication interface may, for instance, be a network interface card (whether wireless or wireless) or a modem. A user interface could, for instance, include one or more user input devices (e.g., a keyboard, a keypad, a touchpad, a stylus, a mouse, or a microphone) and/or one or more user output devices (e.g., a monitor, a display, or a speaker). In general, communication interface 820 may include any combination of devices by which a computer system can receive and output information.

Memory 830 may, for example, include random access memory (RAM), read-only memory (ROM), and/or disc memory. Various items may be stored in different portions of the memory at various times. Memory 830, in general, may be any combination of devices for storing information.

Memory 830 includes instructions 832 and data 834. Instructions 832 may, for example, include an operating system (e.g., Windows, Linux, or Unix) and one or more applications, which may be responsible for analyzing retina images to identify various portions of the retina (e.g., optic disc, fovea, blood vessels, etc.) and performing an identification check based on these. Data 834 may include the data required for the identification check (e.g., the biometric data to be authenticated against). In some implementations, a database of biometric factors may be located remotely from computer system 800.

Network system 840 is responsible for communicating information between processor 1610, input-output system 820, and memory 830. Network system 840 may, for example, include a number of different types of busses (e.g., serial and parallel).

In certain modes of operation, computer system 800 may receive a retina image through input-output system 820. The image may be stored in data 834. Processor 810 may then analyze the image to identify the retina components. Processor 810 may also calculate data regarding the retina components (e.g., position, spacing, neighbors, etc.). Using this data, processor 810 may determine whether the calculated retina data corresponds to pre-stored retina data, which may be stored in a database in data 834. If the calculated retina data corresponds to the pre-stored retina data, processor 810 may generate an access grant message (e.g., a signal, an instruction, and/or a user notification), which may be used inside the computer system or sent to a remote device through input-output system 820.

Processor 810 may also determine whether blood is flowing in the blood vessels of the retina being scanned. If there is blood flowing in the blood vessels of the retina being scanned, processor 810 may allowing access to be granted. If there is not blood flowing in the blood vessels of the retina being scanned, processor 810 may deny access.

Processor 810 may implement any of the other procedures discussed herein, to accomplish these operations.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modification and variations will be apparent to those of ordinary skill in the art without departing from the scope and spirit of the disclosure. The implementations were chosen and described in order to explain the principles of the disclosure and the practical application and to enable others or ordinary skill in the art to understand the disclosure for various implementations with various modifications as are suited to the particular use contemplated.

A number of implementations have been described for biometric identification via retina scanning, and several others have been mentioned or suggested. Moreover, those skilled in the art will readily recognize that a variety of additions, deletions, modifications, and substitutions may be made to these implementations while still achieving biometric identification via retina scanning. Thus, the scope of the protected subject matter should be judged based on the following claims, which may capture one or more concepts of one or more implementations.

The invention claimed is:

1. A system for biometric identification via retina scanning with liveness detection, the system comprising:
  an image acquisition subsystem including at least one narrow-band laser, the image acquisition system adapted to acquire at least one non-mydriatic image of retinal vasculature and to acquire a series of non-mydriatic laser speckle pattern retinal images;

an image analysis subsystem comprising one or more processors adapted to:
analyze the retinal vasculature image to identify retina blood vessels and generate a map thereof;
identify a plurality of components of the retina blood vessels;
calculate a data set that represents the identified components;
compare the calculated data set representing the components against at least one pre-stored data set representing retina components;
determine whether the calculated data set corresponds to the pre-stored data set;
analyze the series of laser speckle images to verify whether the imaged retina is composed of live tissue by determining if variations in speckle pattern in the series of laser speckle images correspond with one or more if the identified blood vessels; and
determine whether to grant access to a resource based on the correspondence of the calculated data set to the pre-stored data set and verification that the imaged retina is composed of live tissue.

2. The system of claim 1, wherein the image acquisition subsystem is adapted to utilize light sources of different wavelengths to obtain at least one non-mydriatic image of retinal vasculature.

3. The system of claim 1, wherein the image analysis subsystem is adapted to determine a number of unique retinal components for identification.

4. The system of claim 1, wherein the image analysis subsystem is adapted to determine whether a predetermined number of components correspond between the pre-stored data set and the calculated data set to determine whether the calculated data set corresponds to the pre-stored data set.

5. The system of claim 1, wherein the image analysis subsystem is adapted to compare the calculated data set against a plurality of data sets representing retina components to compare the calculated data set representing the components against at least one pre-stored data set representing retina components.

6. The system of claim 1, wherein:
the image acquisition subsystem is adapted to detect changes in retina blood flow through retina blood vessels over a period of time; and
the image analysis subsystem is adapted to further verify liveness of the imaged retina by determining whether blood flow in an identified retina blood vessel varies over time in accordance with a cardiac cycle.

7. The system of claim 6, wherein the image analysis subsystem determines whether the blood flow in the identified retina blood vessel increases and decreases over time in accordance with a cardiac cycle to determine whether blood flow varies over time in accordance with a cardiac cycle.

8. The system of claim 1, wherein:
the image acquisition subsystem is adapted to differentially image veins and arteries in the imaged retina based on absorptive and reflective characteristics thereof; and
the image analysis subsystem is adapted to further verify liveness of the imaged retina by determining whether at least one vein and one artery exist in the imaged retina.

9. The system of claim 1, wherein the image analysis system is further adapted to verify whether the imaged retina is composed of live tissue by determining whether the variations in speckle pattern occur only in expected portions of the retina.

10. The system of claim 8, wherein the image analysis subsystem is adapted to analyze the imaged veins and arteries in the imaged retina to further verify whether the imaged retina is composed of live tissue by determining whether the imaged veins and arteries correspond to a previously stored map of veins and arteries in the imaged retina.

11. The system of claim 1, further comprising a security control subsystem adapted to grant access to the resource if the calculated data set matches to the pre-stored data set and the imaged retina is verified to contain living tissue.

12. A method for biometric identification via retina scanning with liveness detection, the method comprising:
scanning a retina with at least one narrow-band laser to acquire at least one non-mydriatic image of retinal vasculature;
illuminating the retina to acquire a series of non-mydriatic laser speckle pattern retinal images;
analyzing the retinal vasculature image to identify retina blood vessels and generate a map thereof;
identifying a plurality of components of the retina blood vessels;
calculating a data set that represents the identified components;
comparing the calculated data set representing the components against at least one prestored data set representing retina components;
determining whether the calculated data set corresponds to the pre-stored data set;
analyzing the series of laser speckle images to verify whether the imaged retina is composed of live tissue by determining if variations in speckle pattern in the series of laser speckle images correspond with one or more of the identified blood vessels; and
determining whether to grant access to a resource based on the correspondence of the calculated data set to the pre-stored data set and verification that the imaged retina is composed of live tissue.

13. The method of claim 12, wherein scanning a retina comprises utilizing light sources of different wavelengths to obtain at least one non-mydriatic image containing retinal vasculature.

14. The method of claim 12, further comprising determining a number of unique retinal components for identification.

15. The method of claim 12, further comprising granting access to the resource if the calculated data set matches the pre-stored data set and the imaged retina is verified to contain living tissue.

16. The method of claim 12, wherein analyzing the series of laser speckle images to verify whether the imaged retina is composed of live tissue comprises determining whether the variations in speckle pattern occur only in expected portions of the retina.

17. The method of claim 12, further comprising:
detecting changes in retina blood flow through retina blood vessels over a period of time; and
further verifying liveness of the imaged retina by determining whether blood flow in an identified retina blood vessel varies over time in accordance with a cardiac cycle.

18. The method of claim 17, further comprising analyzing the imaged veins and arteries in the imaged retina to further verify whether the imaged retina is composed of live tissue by determining whether the imaged veins and arteries correspond to a previously stored map of veins and arteries in the imaged retina.

19. The method of claim 12, further comprising:
differentially imaging veins and arteries in the imaged retina based on absorptive and reflective characteristics thereof; and
further verifying liveness of the imaged retina by determining whether at least one vein and one artery exist in the imaged retina.

* * * * *